(12) United States Patent
Anslyn et al.

(10) Patent No.: US 7,514,266 B2
(45) Date of Patent: Apr. 7, 2009

(54) SYNTHETIC RECEPTORS FOR THE DETECTION OF ANALYTES

(75) Inventors: Eric V. Anslyn, Austin, TX (US); Aaron T. Wright, Austin, TX (US); Zhenlin Zhong, Hubei (CN)

(73) Assignee: Board of Regents, The University of Texas System, Austin, TX (US)

( * ) Notice: Subject to any disclaimer, the term of this patent is extended or adjusted under 35 U.S.C. 154(b) by 130 days.

(21) Appl. No.: 11/172,276

(22) Filed: Jun. 30, 2005

(65) Prior Publication Data

US 2006/0024834 A1 Feb. 2, 2006

Related U.S. Application Data

(60) Provisional application No. 60/584,615, filed on Jun. 30, 2004.

(51) Int. Cl.
*G01N 33/533* (2006.01)
*C07C 211/13* (2006.01)

(52) U.S. Cl. ...................................... 436/140; 564/305
(58) Field of Classification Search .................. 562/7; 436/93, 140; 564/305; 426/93
See application file for complete search history.

(56) References Cited

OTHER PUBLICATIONS

Kayser et al., Tetrahedron, 1997, 53(7), pp. 2475-2484.*
Cai, Shenshen, et al., "A Selective Protein Sensor for Heparin Detection", *Analytical Biochemistry*, 326:33-34, 2004.
Chow, Hak-Fun et al., "A Highly Selective Synthesis of Diarylethynes and their Oligomers by a Palladium-Catalyzed Sonogashira Coupling Reaction under Phase Transfer Conditions", *J. Org. Chem*, 66:1910-1913, 2001.
Gelman, Dmitri et al., "Palladium-Catalyzed Cross-Alkynylation of Aryl Bromides by Sodium Tetraalkynylaluminates", *J. Org. Chem*, 67:6287-6290, 2002.
Pena, Miguel et al., "Multifold and Sequential Cross-Coupling Reactions with Indium Organometallics", *Chemical Communications*, 19:2246-2247, 2002.
Songkram, Chalermkiat et al., "Structures of bis- and tris (2-phenyl-o-carboran-1-yl)benzenes.Construction of Three-Dimensional Structures Converted from Planar Arylacetylenic Arrays", *Tetrahedron Letters*, 42:6365-6358, 2001.
Tobey, S. L. et al., "Determination of Inorganic Phosphate in Serum and Saliva using a Synthetic Receptor", *Organic Letters*, 5:2029-2031, 2003.
Wright, Aaron T. et al., "A Functional Assay for Heparin in Serum using a Designed Synthetic Receptor", *Angewwandte Chemie Int. Ed.*, 44:5679-5682, 2005.
Zhong, Z. et al., "Controlling the Oxygenation Level of Hemoglobin by using a Synthetic Receptor for 2, 3-Bisphosphoglycerate", *Angewandte Chemie Int. Ed.*, 42:3005-3008, 2003.
Zhong, Z., et al., "A Colorimetric Sensing Ensemble for Heparin", *J. Am. Chem. Soc.*, 124:9014-9015, 2002.

* cited by examiner

*Primary Examiner*—Kamal A Saeed
*Assistant Examiner*—Yong Chu
(74) *Attorney, Agent, or Firm*—Baker Botts L.L.P.

(57) ABSTRACT

Synthetic receptor cores are provided that comprise a compound represented by the following formula:

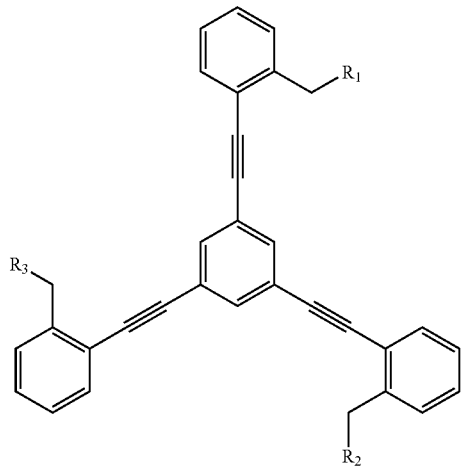

wherein $R_1$, $R_2$, and $R_3$ independently comprise at least one moiety chosen from a hydroxyl group, an amine group, and derivatives thereof. Synthetic receptor cores are provided that comprise a compound represented by the following formula:

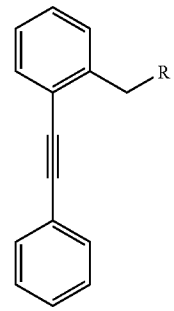

wherein R comprises at least one moiety chosen from a hydroxyl group, an amine group, and derivatives thereof. Synthetic receptors are provided that comprise a synthetic receptor core; and an analyte binding moiety, wherein the analyte binding moiety is capable of complexion with an analyte. Systems, methods, and kits are also provided that use a synthetic receptor.

16 Claims, 7 Drawing Sheets

(A)

(B)

SYNTHETIC RECEPTORS FOR THE DETECTION OF ANALYTES

CROSS-REFERENCE TO RELATED APPLICATION

This Application claims priority to commonly owned United States Provisional Patent Application Ser. No. 60/584,615; filed June 30, 2004; entitled "Synthetic Fluorescent Receptor for the Detection of Heparin" which is incorporated herein by reference.

STATEMENT OF GOVERNMENT INTEREST

This invention was made in part with government support under Grant No. 9 R01 EB00549-04A1 awarded by The National Institute of Health (NIH). The United States government may have certain rights in this invention.

BACKGROUND

The present disclosure, according to one embodiment, relates to compositions and methods for detecting molecules in a sample using a synthetic receptor core molecule.

A common objective when developing synthetic receptors is high binding affinity and specificity for an analyte. This often may be challenging when targeting a complex analyte in a competitive crude medium such as a biological specimen (e.g., serum, urine, or saliva). See S. L. Tobey & E. V. Anslyn, *Org. Lett.* 5:2029-31(2003); Z. Zhong & E. V. Anslyn, *Angew. Chem.* 115:3113-16 (2003).

One example of an analyte for a synthetic receptor is heparin. Heparin is a heterogeneous mixture of diverse chain lengths consisting of repeating copolymers of 1→4 linked iduronic acid and glucosamine residues in a semi-random order. For a biopolymer, heparin has a very high anionic charge to mass ratio, as a result of numerous sulphate and carboxylate functionalities in the biopolymer chain.

In general, two forms of heparin are in clinical use, unfractionated heparin (UFH) with a molecular weight range of from about 3,000 to about 30,000 Da, and low-molecular-weight heparin (LMWH) with a mean molecular weight of about 5,000 Da. During surgery, and in post-operative therapy, heparin concentration and activity is monitored to prevent complications such as hemorrhaging.

Heparin's anticoagulant activity occurs by binding to antithrombin III, a naturally occurring protease inhibitor, accelerating the rate of inhibition of coagulation proteases factor Xa and thrombin by antithrombin III. Clinically administered heparin binds to its natural substrate antithrombin III primarily through cationic ion-pairing interactions with the sulphates and carboxylates. Similarly, the cationic protein protamine is another ligand for heparin.

Current methods for heparin quantification employ the Activated Clotting Time (ACT), Activated Partial Thromboplastin Time (aPTT), chromogenic anti-factor Xa assay, electrochemical and piezoelectric assays, and complexation with protamine. Nonclinically, heparin also has been quantified using an engineered GST-fusion protein containing three hyaluronan-binding domains from a heparin binding protein, but it has not been employed clinically. J. L. Cai, et al., *Anal. Biochem.* 326:33-4 (2004). These methods may be problematic, however, as they may be difficult, inaccurate, costly, and not amenable to clinical settings.

SUMMARY

In general, the present invention provides synthetic receptor core compositions, synthetic receptor compositions that have a moiety that is capable of interacting with an analyte (an "analyte binding moiety"), and systems and methods that use these compositions. The compositions of the present invention may be used, or modified to be used, for example, as synthetic receptors with high affinity and specificity for an analyte of interest. In addition, the synthetic receptor cores of this disclosure may provide a basis on which a receptor specific to a desired analyte may be formed. Such cores may be capable of fluorescence, and therefore may be useful to form synthetic receptors suitable for, among other things, high affinity, specific binding of a target analyte. In operation, such synthetic receptors may have a fluorimetric spectrum that may be detectably altered upon formation of a complex comprising the synthetic receptor and an analyte. Accordingly, such synthetic receptor compositions may be employed, for example, as chemosensors, and in methods and systems to detect and quantify an analyte.

According to a specific example embodiment of this disclosure, synthetic receptor cores are provided that comprise a compound represented by the following formula:

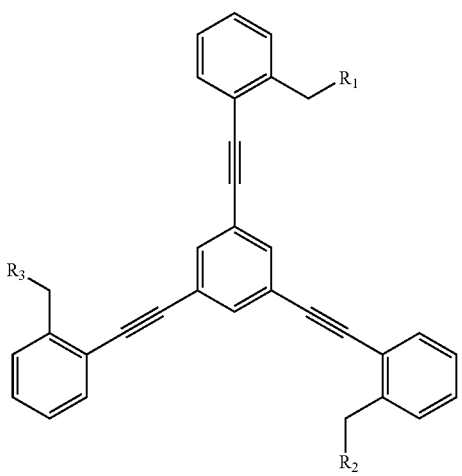

wherein $R_1$, $R_2$, and $R_3$ independently comprise at least one moiety chosen from a hydroxyl group, an amine group, and derivatives thereof.

According to another specific example embodiment of this disclosure, synthetic receptor cores are provided that comprise a compound represented by the following formula:

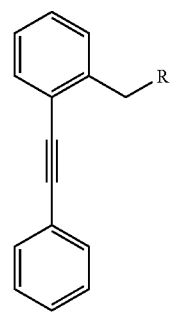

wherein R comprises at least one moiety chosen from a hydroxyl group, an amine group, and derivatives thereof.

According to another specific example embodiment of this disclosure, synthetic receptor cores are provided that comprise a 1,3,5 tris-(phenylethynyl)benzene molecule; and at least one functional group chosen from a benzylic alcohol and a benzylic amine attached to the 1,3,5 tris-(phenylethynyl) benzene molecule by derivatization of the 1,3,5 tris-(phenylethynyl)benzene molecule.

According to another specific example embodiment of this disclosure, synthetic receptor cores are provided that comprise a diphenylacetylene molecule; and at least one functional group chosen from a benzylic alcohol and a benzylic amine attached to the diphenylacetylene molecule by derivatization of the diphenylacetylene molecule.

According to another specific example embodiment of this disclosure, synthetic receptors are provided that comprise a synthetic receptor core; and an analyte binding moiety, wherein the analyte binding moiety is capable of complexion with an analyte.

According to another specific example embodiment of this disclosure, systems are provided that comprise a sample chamber comprising: a sample disposed within the sample chamber; and a plurality of synthetic receptor molecules disposed within the sample chamber, wherein the plurality of synthetic receptor molecules comprise: a synthetic receptor core; and an analyte binding moiety, wherein the analyte binding moiety is capable of complexion with an analyte; a photon source disposed operative with the sample chamber to provide photons to the sample chamber; and a photon detector disposed operative with the sample chamber to provide detection of photons from the sample chamber.

According to another specific example embodiment of this disclosure, kits are provided that comprise a synthetic receptor, wherein the wherein the synthetic receptor comprises: a synthetic receptor core; and an analyte binding moiety, wherein the analyte binding moiety is capable of complexion with an analyte; a container for a sample; one or more containers for combining the synthetic receptor and the sample.

According to another specific example embodiment of this disclosure, synthetic receptor cores and synthetic receptors may be fluorimetric. Such compositions may be used in, among other things, methods for the detection of an analyte, for example, heparin, in a sample, for example a biological sample (e.g. serum). Such methods may be advantageous in that they may have minimal sample and synthetic receptor requirements for testing, as well as be a rapid and efficient method for analyte detection or quantification or both.

The development of synthetic receptors may be based on a synthetic core receptor which is transformed to allow high binding affinity and specificity for an analyte while retaining the core elements of the receptor (for example, fluorescent properties). Transformation may involve chemical derivation of the core receptor molecule so as to alter the molecular spacing of the target binding portions of the molecule. The present disclosure, in one embodiment, adopts this approach to provide for compositions and methods useful for specific binding and detection of heparin in a sample using fluorescent receptor molecules.

DRAWINGS

A more complete understanding of the present disclosure may be acquired by referring to the following description taken in conjunction with the accompanying drawings.

Figure 4A:
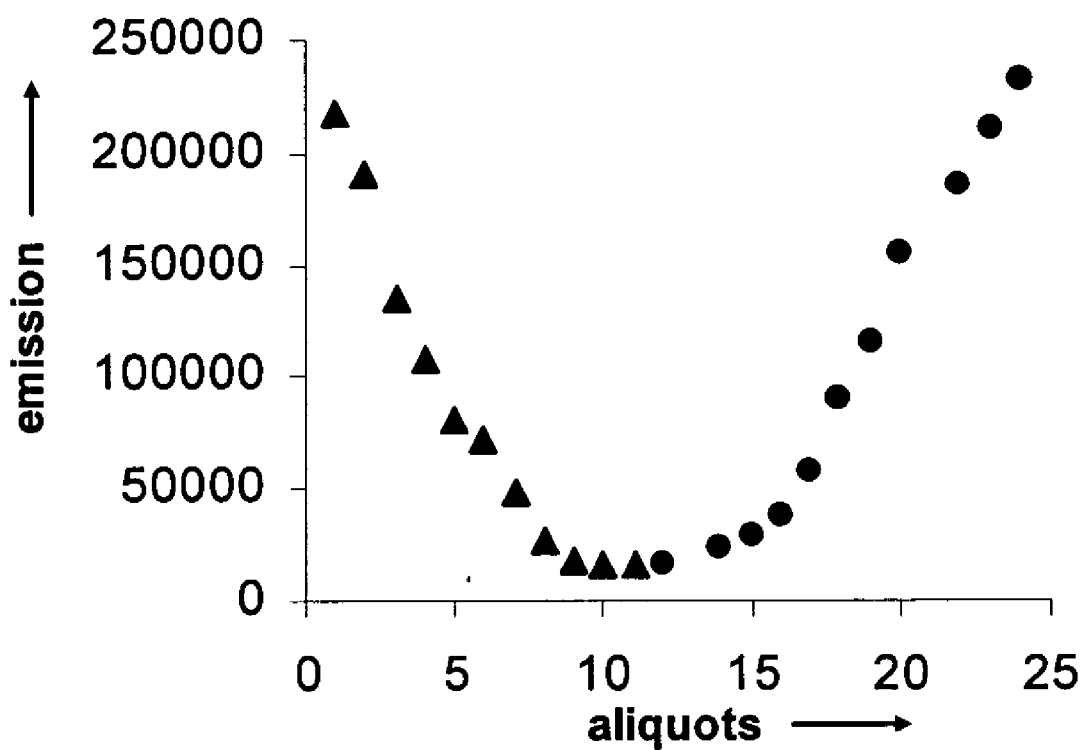

FIG. 4(A) is a graph of emissions followed at 357 nm showing reversibility of LMWH:synthetic receptor binding upon titration with protamine, according to a specific example embodiment of this disclosure. First 11 aliquots of heparin are added (▲), and last 12 aliquots are addition of protamine (●). The aliquots were diluted with buffered water (HEPES, pH=7.4). The fluorescent emission is reestablished upon titration.

Figure 4B:
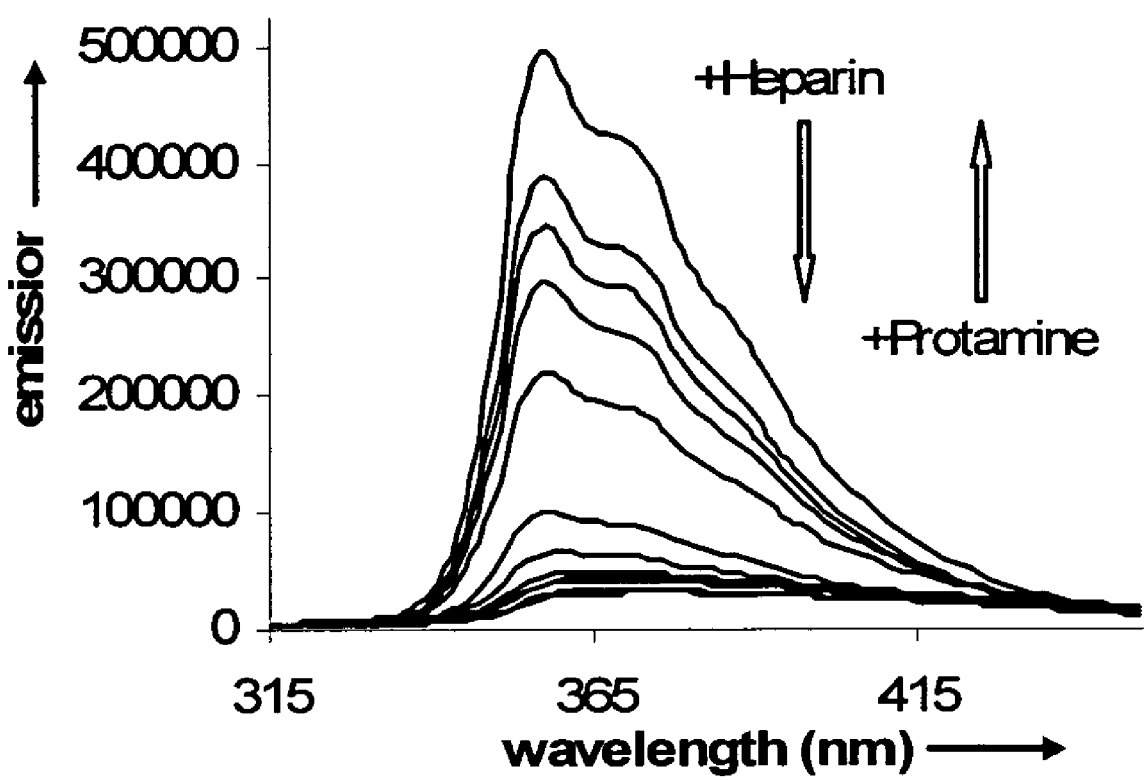

FIG. 4(B) is a graph of emission spectrum of a synthetic receptor, according to a specific example embodiment of this disclosure, upon addition of LMWH showing addition of protamine reverses the spectrum.

Figure 5:
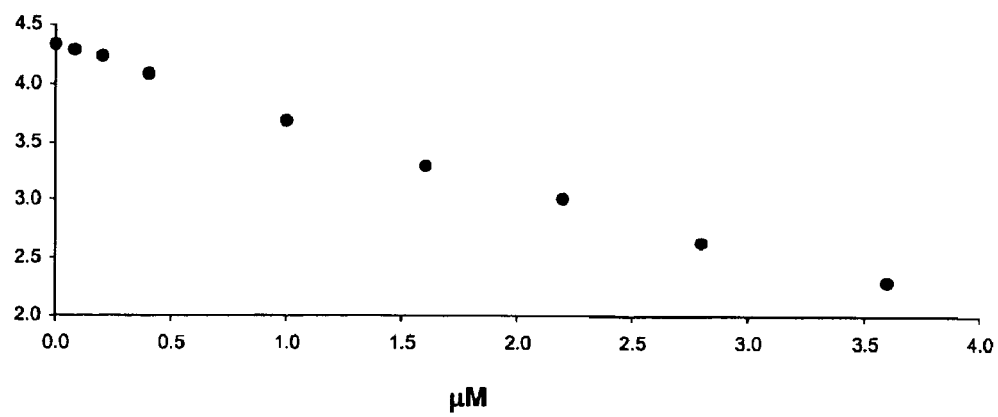
Figure 5:
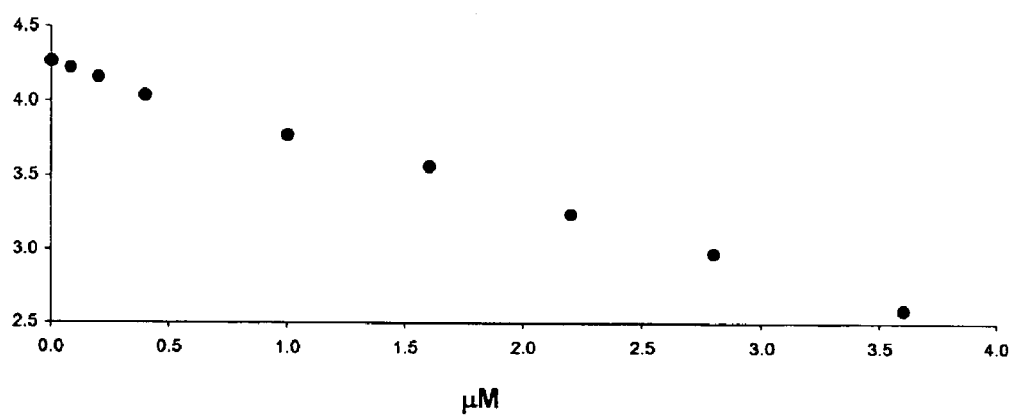

FIG. 5 is a graph showing calibration curves for LMWH (A) and UFH (B) in human serum, according to a specific example embodiment of this disclosure. Conformational changes to a synthetic receptor upon binding to heparin result in a diminished fluorescence emission at 357 nm. Greater concentrations of UFH and LMWH correspond to increases in fluorescent quenching. For both UFH and LMWH, the range of detection was from 0-9 U/mL (0-3.6 μM).

Figure 6:
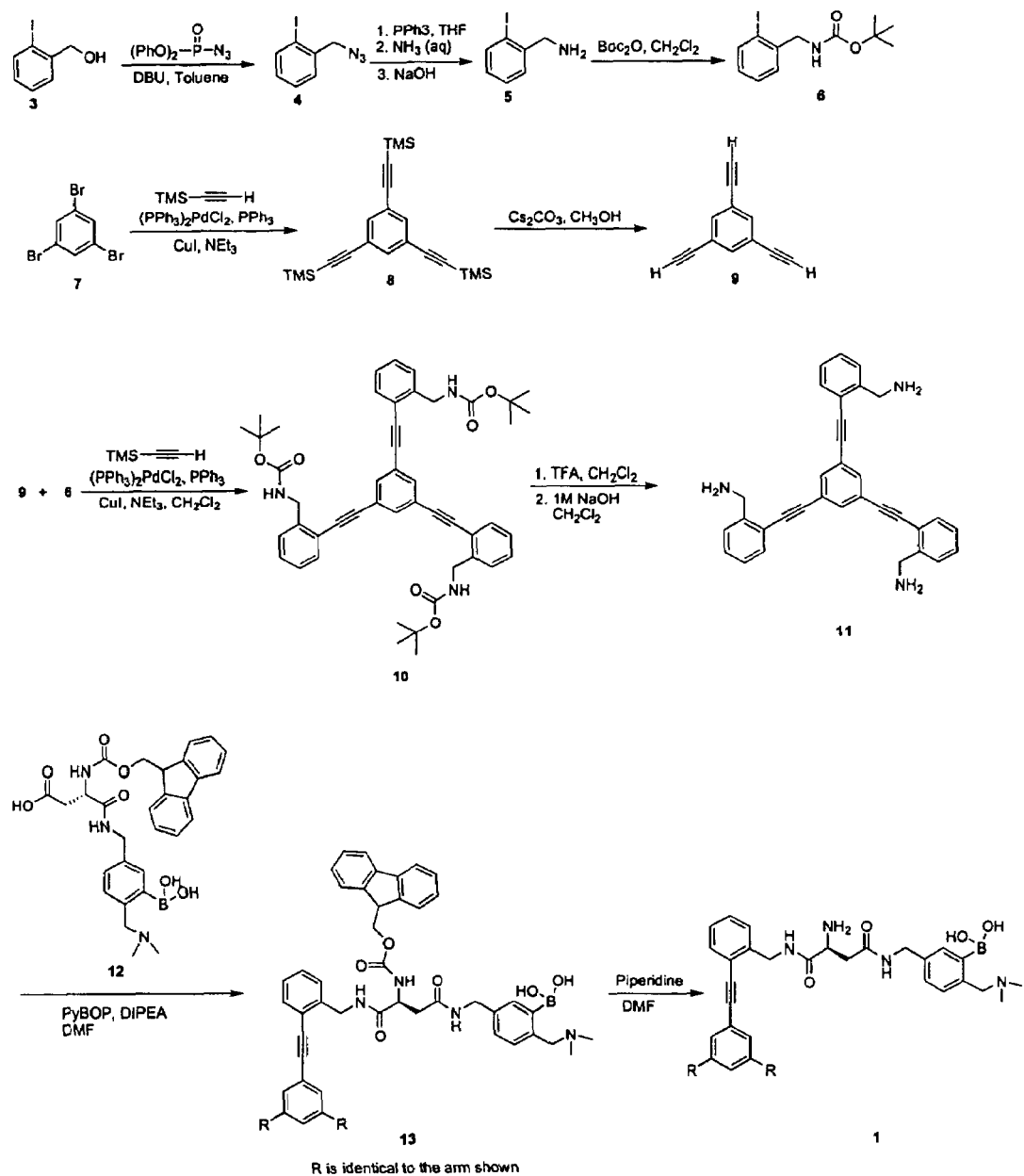

FIG. 6 is a synthetic scheme for the synthesis of a synthetic receptor, according to a specific example embodiment of this disclosure.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

DESCRIPTION

According to one embodiment, a synthetic receptor core composition of the present disclosure may be represented by Formula I:

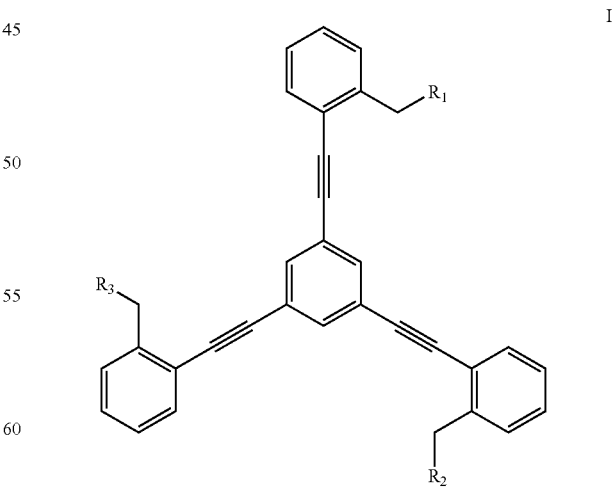

wherein $R_1$, $R_2$, and $R_3$ independently comprise at least one moiety chosen from a hydroxyl group, an amine group, and derivatives thereof. Such a synthetic receptor core may be formed by derivatizing a 1,3,5 tris-(phenylethynyl)benzene molecule with a functional group, such as a benylic alcohol, a benzylic amine, or a derivative thereof.

According to another embodiment, a synthetic receptor core composition of the present disclosure may be represented by Formula II:

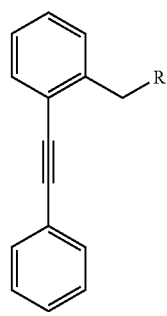

II wherein R comprises at least one moiety chosen from a hydroxyl group, an amine group, and derivatives thereof. Such a synthetic receptor core may be formed by derivatizing a diphenylacetylene molecule with a functional group, such as a benylic alcohol, a benzylic amine, or a derivative thereof.

In general, synthetic receptor core molecules may be derivatized. For example, synthetic receptor core molecules may be oxidized to form, among other things, aldehydes and carboxylic acids. Synthetic receptor core molecules also may be derivatized to form esters and ethers. For synthetic receptor core molecules that comprise a hydroxyl group, the hydroxyl group may derivatized by converting the hydroxyl group into a good leaving group and allowing the good leaving group to undergo a substitution reaction. Other examples of suitable derivatizations include, but are not limited to, alkylations (e.g., using alkyl halides) and arylations (e.g., using aryl halides).

In some embodiments, $R_1$, $R_2$, and $R_3$ of Formula I and R of Formula II may comprise an amide bond, an amino acid, or both. In other embodiments, $R_1$, $R_2$, and $R_3$ of Formula I and R of Formula II may comprise a guanidinium molecule, for example, to form a cationic binding cavity. In yet other embodiments, $R_1$, $R_2$, and $R_3$ of Formula I and R of Formula II may comprise a diacid (e.g., succinic acid), among other things, to aid in further derivatizations.

In some applications, a spacer may be useful to include on a synthetic receptor core. Such spacers may be used, among other things, to change the spacing between a synthetic receptor core and an analyte binding domain or moiety present on a synthetic receptor. By way of explanation, and not of limitation, changing the spacing in this way may allow for a change in a synthetic receptor's analyte specificity. Accordingly, the synthetic receptor core may further comprise a spacer. And examples of suitable spacers include, but are not limited to, glutamic acid, cysteine, serine, tyrosine, lysine, histidine, threonine, and arginine.

In general, the synthetic receptor cores of the present disclosure represented by Formula I may be formed by derivatizing 1,3,5 tris-(phenylethynyl)benzene with a benzylic alcohol by coupling a benzyl alcohol to 1,3,5 tris-(phenylethynyl)benzene (e.g., through a platinum catalyzed coupling reaction). Such a derivatization may form a synthetic receptor core represented by Formula I in which $R_1$, $R_2$, and $R_3$ independently may comprise a hydroxyl group. Subsequent derivitizations may be used to form still other synthetic receptor cores and synthetic receptors of the present disclosure that have an analyte binding moiety. For example, by further substituting the benzyl alcohol with a benzyl amine a synthetic receptor core represented by Formula I may be formed in which $R_1$, $R_2$, and $R_3$ independently may comprise an amine group, which may be further derivatized to form still other synthetic receptor cores and synthetic receptors of the present disclosure that have an analyte binding moiety.

Similarly, the synthetic receptor cores of the present disclosure represented by Formula II may be formed by derivatizing diphenylacetylene with a benzylic alcohol by coupling a benzyl alcohol to the diphenylacetylene (e.g., through a platinum catalyzed coupling reaction). Such a derivatization may form a synthetic receptor core represented by Formula II in which R may comprise a hydroxyl group. Subsequent derivitizations may be used to form still other synthetic receptor cores and synthetic receptors of the present disclosure that have an analyte binding moiety. For example, by further substituting the benzyl alcohol with a benzyl amine a synthetic receptor core represented by Formula II may be formed in which R may comprise an amine group, which may be further derivatized to form still other synthetic receptor cores and synthetic receptors of the present disclosure that have an analyte binding moiety.

According to another embodiment, the synthetic receptor cores of the present disclosure may be covalently bound to a solid phase support. Such compositions may be useful, among other things, to form materials useful for screening chemical libraries using, for example, combinatorial chemistry. Examples of suitable solid phase supports include, but are not limited to, silica gels, resins, derivatized plastic films, multi-well assay plates, glass, glass beads, fiber optics, cotton, plastic beads, alumina gels, synthetic antigen-presenting matrices, cells, and liposomes. In some examples, in which the synthetic receptor core comprises a compound according to Formula I, the solid phase support may be covalently bound to one or more of $R_1$, $R_2$, and $R_3$.

As mentioned above, the synthetic receptor cores of the present disclosure may be used to form synthetic receptors. Such synthetic receptors generally comprise a synthetic receptor core and an analyte binding moiety. The analyte binding moiety may be capable of forming a complex with a desired analyte, for example, heparin. In this way, synthetic receptors of the present disclosure may be used to detect the analyte, for example, through fluorescence quenching or a change in the UV-Vis spectrum. For example, the binding of an analyte (e.g., heparin) with a synthetic receptor that comprises a binding moiety capable of forming a complex with the analyte may cause a decrease in the emission spectra of the synthetic receptor, which may result in a near complete quenching of the synthetic receptor's emission spectrum. By detecting this quenching the amount of analyte present in a sample may be determined, among other things.

Various synthetic receptors of the present invention may be formed using the synthetic receptor cores of the present disclosure, depending on, for example, the analyte binding moiety chosen. Any analyte binding moiety may be chosen based on, for example, the degree of specificity for an analyte, the strength of complexation with the analyte, the desired application, and the like. Examples of analytes with which a binding moiety may complex include, but are not limited to, inositol trisphosphate, glycosaminoglycans (e.g., chondroitin-4-sulfate and hyaluronic acid), small peptides, peptoids (i.e. hormones), proteins (including glycoproteins and phosphorylated and sulfated proteins), anionic species, and cationic species.

One example of a synthetic receptor of the present disclosure is the synthetic receptor represented by Formula III:

III

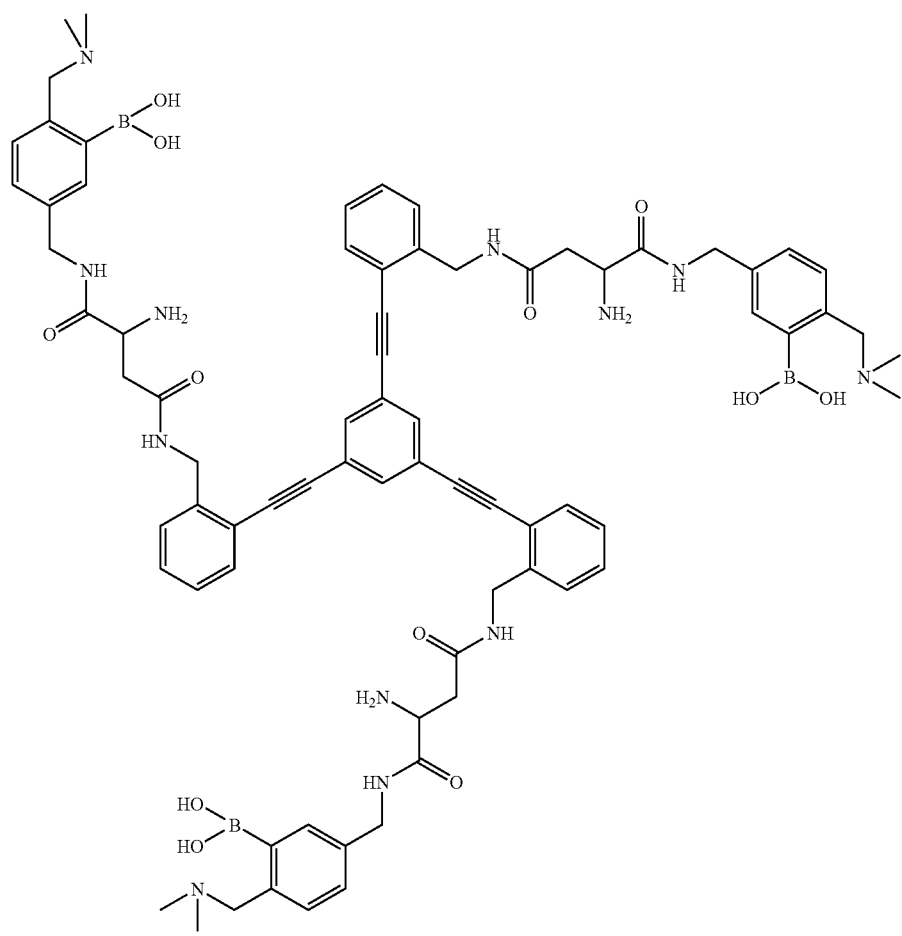

This synthetic receptor may be capable of forming a complex with heparin, and may have a fluorimetric spectrum that may be detectably altered upon formation of a complex comprising the receptor and a heparin molecule. Accordingly, this synthetic receptor may be used to detect heparin in a sample, as describe herein.

According to another embodiment, the synthetic receptors of the present disclosure may be used in methods for detecting an analyte in a sample. Such methods may comprise providing a sample that may comprise an analyte; contacting a synthetic receptor to the sample; allowing the formation of a synthetic receptor-analyte complex; and identifying the formation of the synthetic receptor-analyte complex. The sample may be obtained from a subject, such as a biological specimen (e.g. blood sera) from a human patient or an animal patient. The sample also may be obtained from a synthetic source, such as a sample from a pharmaceutical product (e.g., heparin). For synthetic receptors having a fluorescent emission, the change in fluorescebt emission that may occur upon complexation with an analyte may be detected and compared to a standard to, for example, determine the concentration of the analyte in the sample being tested.

According to another embodiment, the synthetic receptors of the present disclosure may be used in methods for detecting an analyte in a sample in which the synthetic receptor is derivatized or immobilize onto a solid phase support. For example, a synthetic receptor may be immobilized onto a fiber optics cable that could then be inserted into a sample (e.g., a serum solution). A fluorescence measurement could then be obtained via the interactions occurring at the tip of the fiber optic cable. This could enhance the rate at which the sample equilibrates by enhancing the speed of interaction between receptor and heparin.

According to a specific example embodiment, the synthetic receptor represented by Formula III may be used in a binding assay for UFH and LMWH. Such an assay may be capable of detecting a binding interaction between the synthetic receptor represented by Formula III and heparin in a sample (e.g. a serum sample) with a resolution in the nM rage. The assay may be performed by monitoring the interaction of the synthetic receptor represented by Formula III with heparin in a sample using fluorescence spectroscopy. By way of explanation, and not of limitation, binding of heparin with the synthetic receptor represented by Formula III may cause a decrease in the emission spectra, resulting in a near complete quenching of the synthetic receptor's emission through a conformational restriction of the synthetic receptor core's acetylene "arms," thereby modulating the fluorescence of the receptor-analyte complex.

The present disclosure, according to certain embodiments, also provides systems for, among other things, the detection of analytes. Such systems may comprise a sample chamber in which a sample that includes the analyte is disposed within, and wherein the sample comprises a plurality of synthetic receptor molecules disposed within the sample chamber; a photon source disposed operative with the sample chamber to provide photons to the sample chamber; and a photon detector disposed operative with the sample chamber to provide detection of photons from the sample chamber. In some embodiments these systems also may comprise a photomultiplier tube, a computer, or both.

The present disclosure, according to certain embodiments, also provides kits for, among other things the detection of analytes. Such kits may comprise a synthetic receptor molecule, a container for a sample; and one or more containers for combining the synthetic receptor and the sample.

To facilitate a better understanding of the present invention, the following examples of specific embodiments are given. In no way should the following examples be read to limit or define the entire scope of the invention.

EXAMPLES

Materials and Methods

General. Reactions were run under an atmosphere of argon unless otherwise indicated. Anhydrous solvents were transferred by an oven-dried syringe. Flasks were flame dried under a stream of argon. Chemicals for synthesis were obtained from Acros Organics, Aldrich, and NovaBiochem and were used without further purification. Methlyene chloride and triethylamine were distilled over calcium hydride. Human and equine sera were purchased from Sigma-Aldrich and used without further purification. Low molecular weight heparin was prepared via oxidative depolymerization, pursuant to pharmaceutical procedures according to Sigma-Aldrich. UFH and LMWH were both employed as their sodium salts, as is common with pharmaceutical therapeutics. A Varian Gemini 400 MHz NMR was used to obtain $^1$H and $^{13}$C spectra. A Finnigan TSQ70 and VG Analytical ZAB2-E mass spectrometers were used to obtain low and high resolution mass spectra respectively. Melting points were measured on a Thomas Hoover capillary melting point apparatus and are uncorrected. All products were dried for at least 6 hours prior to spectral analysis. Fluorescent measurements were performed on a Photon Technology International Fluorimeter (LPS-220B, MB-5020, PMT-814).

Synthesis of a Synthetic Receptor According to a Specific Example Embodiment of the Present Disclosure One example of the synthesis of an HR1 synthetic receptor is as follows and depicted in FIG. 6. Bolded numbers in parenthesis refer to synthesis intermediates in the synthetic scheme for HR1 as shown in FIG. 6/

(4) 2-iodo-benzylazide. 1,8-Diazabicyclo[5,4,0]undec-7-ene (5.55 mmol, 1.3 eq) was added to a solution of 2-iodo-benzylalcohol (4.27 mmol, 1.0 eq) and diphenylphosphoryl azide (5.13 mmol, 1.2 eq) in 9 mL toluene under argon. The reaction ran at room temperature for 1.25 hours. At this time 3 N HCl (9 mL) was added and stirred briefly. The solution was extracted with ether, and the organic layer was washed successively with water (3×15 mL) and saturated NaCl (2×15 mL). The organic layer was dried with sodium sulfate, filtered, and removed in vacuo. Obtained a clear oil in 65% yield that was used without further purification. $^1$H NMR (400 MHz, CDCl$_3$) δ 7.91 (d, 1H), 7.42 (d, 1H), 7.41 (t, 1H), 7.06 (t, 1H), 4.48 (s, 2H). $^{13}$C NMR (100 MHz, CDCl$_3$) δ 139.4, 137.8, 129.7, 129.2, 128.4, 98.9, 58.7. MS (CI+) m/z 232 ([M-N$_2$]$^+$)

(5) 2-iodo-benzylamine. To a solution of (4) (2.75 mmol, 1 eq) in dry THF (5 mL) under argon was added triphenylphosphine (3.06 mmol, 1.11 eq) portion wise. This reaction stirred 16 hours, upon completion aqueous ammonia was added. This stirred 3 hours at which 3 N NaOH (20 mL) was added and stirred 1 hour. The solution was then neutralized with 2 N HCl (30 mL) and extracted with ether. The organic layer was washed with water (2×25 mL) and brine (2×25 mL). The organic layer was dried with sodium sulfate, filtered, and removed in vacuo. A yellow oil was obtained, which was not purified and was immediately used in the subsequent step.

(6) (2-iodo-benzyl)-carbamic acid tert-butyl ester. To crude (5) in THF (15 mL) was added di-tert-butyldicarbonate (3.66 mmol, 1.33 eq). This solution was stirred vigorously for 6 hours. Upon completion ether was added (10 mL). The organic layer was washed with water (2×25 mL) and brine (2×25 mL), dried with sodium sulfate, filtered, and removed in vacuo. The product was further purified on a SiO$_2$ column (2% ethyl acetate in hexanes). Product collected as off-white powder (2.16 mmol) in 79% yield and had a melting point of 54-56° C. $^1$H NMR (400 MHz, CDCl$_3$) δ 7.79 (d, 1H), 7.34 (d, 1H), 7.31 (t, 1H), 6.94 (t, 1H), 4.31 (d, 2H), 1.44 (s, 9H). $^{13}$C NMR (100 MHz, CDCl$_3$) δ 155.6, 140.8, 139.2, 128.9, 128.4, 98.6, 79.5, 49.2, 28.3. MS (CI+) m/z 233.8 [M]$^+$.

(8) 1,3,5-tris-trimethylsilanylethynyl-benzene. To flame-dried, argon-purged flask with condenser was added 1,3,5-tribromobenzene (5.08 mmol, 1 eq), Pd(PPh)$_3$Cl$_2$ (0.051 mmol, 0.01 eq), CuI (0.051 mmol, 0.01 eq), and triphenylphosphine (0.051 mmol, 0.01 eq) in distilled triethylamine (10 mL). This solution mixed for 20 minutes at 85° C. To the solution was added trimethylsilylacetylene (20.8 mmol, 4.1 eq). The reaction stirred for 4 hours. Upon completion the reaction was cooled to room temperature, diluted with hexanes, and filtered through Celite 545. The organic layer was removed in vacuo. The product was further purified on a SiO$_2$ column (petroleum ether). Obtained an off-white solid (3.03 mmol) in 60% yield and had a melting point of 78-80° C. $^1$H NMR (400 MHz, CDCl$_3$) δ 7.54 (s, 3H), 0.29 (s, 27H). $^{13}$C NMR (100 MHz, CDCl$_3$) δ 135.1, 123.8, 103.3, 95.7, 0.0. MS (CI+) m/z 367 [M]$^+$.

(9) 1,3,5-trisethynyl-benzene. To a flame-dried flask under argon was added (8) (2.39 mmol, 1 eq), cesium carbonate (4.78 mmol, 2 eq), and methanol (10 mL). The reaction was stirred 16 hours. The solution went from opaque to translucent upon completion. The methanol was removed in vacuo and the solid was partitioned between water and methylene chloride. The water layer was extracted with methylene chloride (3×20 mL). The organic layer was washed with aqueous ammonium chloride (1.0 M, 2×20 mL), water (2×20 mL), and brine (2×20 mL). The organic layer was dried with sodium sulfate, filtered, and removed in vacuo. Product obtained as off-white soft crystals (2.09 mmol) in 87% yield and had a melting point of 101-103° C. $^1$H NMR (400 MHz, CDCl$_3$) δ 7.57 (s, 3H), 3.12 (s, 3H). $^{13}$C NMR (100 MHz, CDCl$_3$) δ 135.6, 122.8, 81.6, 78.7. MS (CI+) m/z 151 [M]$^+$.

(10) (2-{3,5-bis [2-(tert-butoxycarbonylamino-methyl)-phenylethynyl]-phenylethynyl}-benzyl)-carbamic acid tert-butyl ester. To a flame-dried, argon-purged flask with condenser was added (6) (1.24 mmol, 4.0 eq), Pd(PPh)$_3$Cl$_2$ (0.006 mmol, 0.02 eq), CuI (0.006 mmol, 0.02 eq), and triphenylphosphine (0.006 mmol, 0.02 eq) in distilled triethylamine (5 mL) and methylene chloride (5 mL). The reaction was set at 60° C and the solution mixed 15 minutes. At this point (9) (0.309 mmol, 1.0 eq) was added, and the reaction ran 16 hours with constant stirring. Upon completion the solvent was removed in vacuo, and the product was purified on a SiO$_2$ column (22% ethyl acetate in hexanes). Product was recrystallized in hexanes with minimal amount of methylene chloride to give a white solid (0.251 mmol) in 81% yield and had a melting point of 77-79° C. $^1$H NMR (400 MHz, CDCl$_3$) δ 7.66 (s, 3H), 7.52 (d, 3H), 7.38 (d, 3H), 7.32 (t, 3H), 7.25 (t, 3H), 5.08 (br, NH), 4.55 (d, 6H), 1.43 (s, 9H). $^{13}$C NMR (100 MHz, CDCl$_3$) δ 155.8, 140.7, 134.1, 132.4, 129.0, 127.8, 127.2, 123.9, 121.5, 92.9, 88.3, 79.5, 43.3, 28.4. MS (CI+) m/z 766 [M]$^+$.

(11) 2-[3,5-bis(2-aminomethyl-phenylethynyl)-phenylethynyl]-benzylamine. To a flame-dried, argon-purged flask was added (10) (0.092 mmol, 1 eq) and methylene chloride (5 mL). The solution was cooled to 0° C. and trifluoroacetic acid (1.35 mmol, 14.7 eq) was dripped into the reaction. The reaction was allowed to slowly warm to room temperature.

After 10 hours the solvents were removed in vacuo. The residue was dissolved in water, basified with 1 N NaOH, and extracted with methylene chloride (2×10 mL). The organic layer was washed with brine (10 mL), dried with sodium sulfate, filtered, and removed in vacuo. A light yellow solid was obtained (0.082 mmol) in 90% yield and had a melting point (decomposed) of 117-121° C. No further purification was necessary. $^1$H NMR (400 MHz, CD$_3$OD) δ 7.79 (s, 3H), 7.60 (d, 3H), 7.59-7.41 (m, 9H), 4.33 (s, 6H). MS (CI+) m/z 466 [M]$^+$. Elemental composition, m/z 465.2 ($C_{33}H_{27}N_3$).

(13) Fmoc-protected heparin receptor. To a solution of (11) (0.054 mmol, 1 eq), (12) (0.215 mmol, 4 eq), and diisopropylethylamine (0.556 mmol, 10 eq) in N,N-dimethylformamide (DMF) (3 mL) was added benzotriazole-1-yl-oxy-trispyrrolidino-phosphonium hexafluorophosphate (PyBOP) (0.215 mmol, 4 eq). The reaction was stirred at room temperature for 3.5 hours. Upon completion the product was precipitated with acetonitrile (15 mL). The product was filtered, redissolved in DMF (3 mL), and precipitated again with acetonitrile (15 mL). This process was repeated twice more. A slightly yellow residue was obtained and used without further purification or characterization in the next step.

(1) Heparin receptor HR1. Dissolved (13) in a solution of 20% piperidine in DMF (2 mL). The reaction was stirred at room temperature for 16 hours. The solvent was removed in vacuo with azeotropic addition of toluene. Product was dried thoroughly on the hi-vac. The crude residue was dissolved in 0.2 M HCl (10 mL) and chloroform (6 mL). This solution stirred for 25 min. The precipitate was filtered and the aqueous layer collected. The aqueous layer was washed with methylene chloride (2×10 mL). The aqueous layer was removed in vacuo; the residue was redissolved in water (2 mL) and removed using a lyophilizer. A slightly off-white solid (0.052 mmol) was collected in 96% yield and had a melting point (decomposed) of 144-148° C. No further purification was necessary, however product contained minimal (3.7%) piperidine impurity. $^1$H NMR (400 MHz, CD$_3$OD) δ 8.23 (d, NH), 7.77 (d, 3H), 7.64 (s, 3H), 7.47-7.21 (m, 18H), 4.31 (br, 12H), 3.31 (m, 3H), 3.02 (br, 6H), 2.94 (br, 6H), 2.79 (s, 18H). MS (ESI) m/z 1328 [M-3(OH), loss of one hydroxyl from each boronic acid induced by N-B bond formation]. MS (CI+) m/z 1328 [M-3(OH)].

Fluorescence Measurements

Binding Constants. In a 2 mL volumetric flask was prepared a HEPES (pH=7.4) buffered solution of HR1 (2.24×10$^{-6}$). 1.50 mL of this solution was placed into a quartz cuvette. To the remaining 0.50 mL solution was added UFH or LMWH (6.66×10$^{-5}$). At this concentration, each 5 μL titration of the heparin solution represents 0.1 equivalents to HR1. From the titration curves, emission data was extracted from only 357 nm and plotted against heparin concentration as shown in the paper. Using Microcal Origin software binding constants were determined to be in the range of 1.0×10$^8$ M$^{-1}$ to 2.0×10$^8$ M$^{-1}$.

Figure 1:
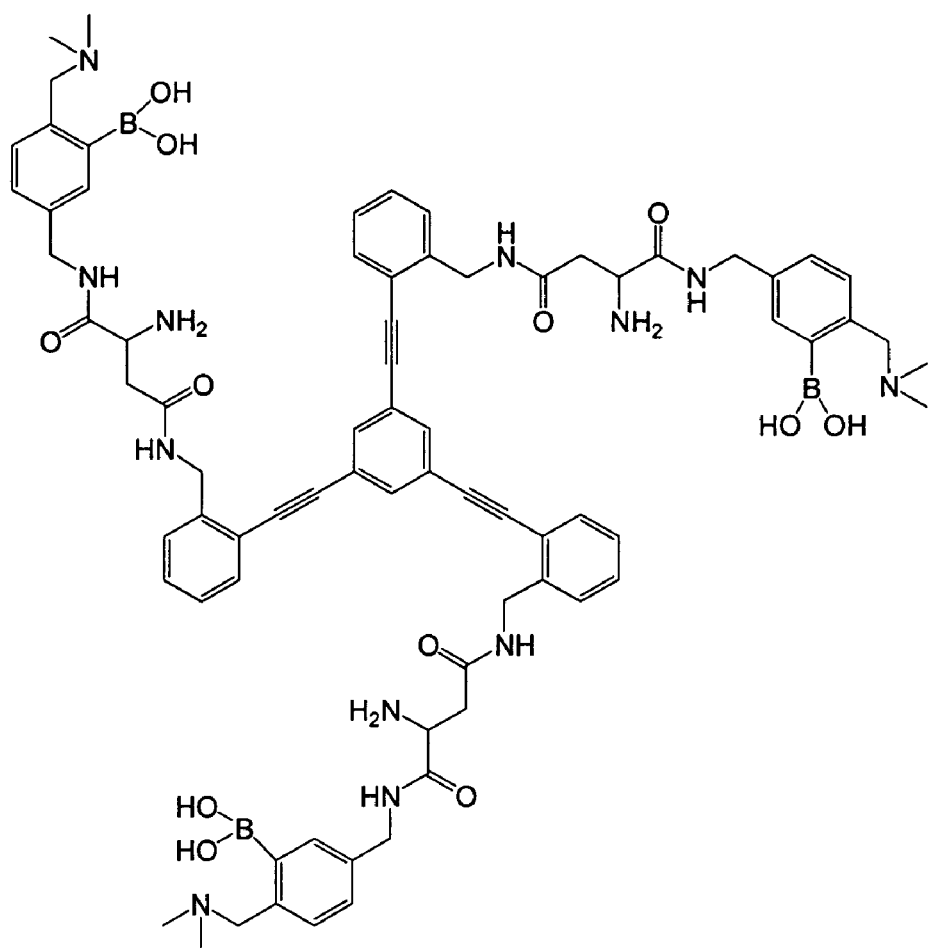
FIG. 1 is a chemical structure of a synthetic receptor, according to a specific example embodiment of this disclosure.
Figure 2:
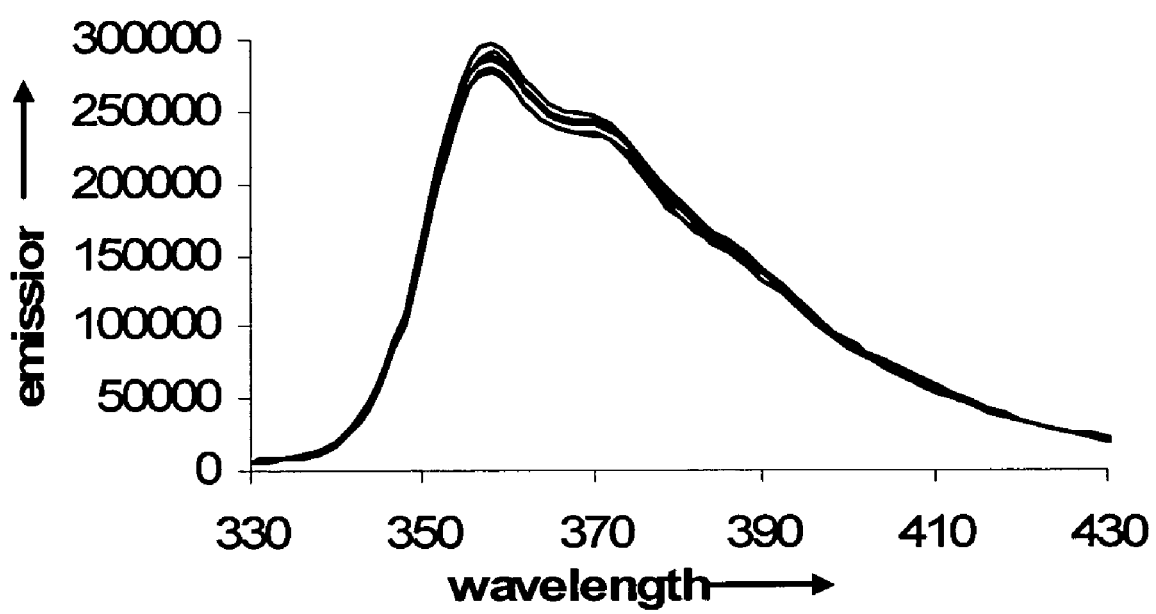
FIG. 2 is a fluorescent emission spectrum a synthetic heparin receptor, according to a specific example embodiment of this disclosure, upon titration of ~0.4 equivalent aliquots of protamine. A total of 2.0 equivalents were added.

Protamine Titrations. As described in the determination of binding constants, a 1:1 heparin:HR1 complex was formed prior to addition of protamine. In the 0.5 mL solution was added protamine (3.33×10$^{-5}$). However, the exact molecular weight of protamine was not known, so this was an approximate concentration. Titration of 10 μL aliquots of the protamine solution reversed the binding between heparin and HR1. Attempts to reverse heparin binding in serum did not work as addition of protamine elicited rapid precipitation of byproducts within the serum. As shown in FIG. 2, there was virtually no change in the fluorescence emission spectrum when HR1 was titrated with protamine alone (~0.4 equivalent aliquots of protamine, and a total of 2.0 equivalents was added). There was no cumulative increase or decrease in the emission spectrum upon protamine titration. This control experiment illustrated that protamine does not simply bind to the receptor and restore the fluorescent emission.

UFH and LMWH Standard Addition Curves

A fluorimetric cell was prepared in the following way: 1398 μL deionized water was added followed by 32 μL of human serum doped with low molecular weight heparin (LMWH—exists therapeutically in several clinical forms such as Lovenox®) or unfractionated heparin (UFH—generally administered during cardiopulmonary surgery). To this was added 100 μL HEPES (0.020 mol/L) to buffer the solution at pH=7.4. Following a 15 second mix period, 2 μL of the receptor (2.24×10$^{-3}$ mol/L) shown above was added. This solution was mixed briefly and then fluorescence emission measurements were obtained every three minutes. At approximately 18 minutes the solution fully stabilized. Reasonable results could have been obtained from 6-9 minutes as well, but were not quite as accurate.

As mentioned above, the human (and equine) serum samples were doped with either LMWH or UFH. Seven vials were prepared with UFH and LMWH concentrations ranging from 0-54 μg/mL. The fluorescent emission response of the receptor decreased at higher heparin concentration levels. This allowed for the development of a standard calibration graph as shown in FIG. 7(A) for LMWH in human serum and in FIG. 7(B) for UFH in human serum.

Results

Figure 3:
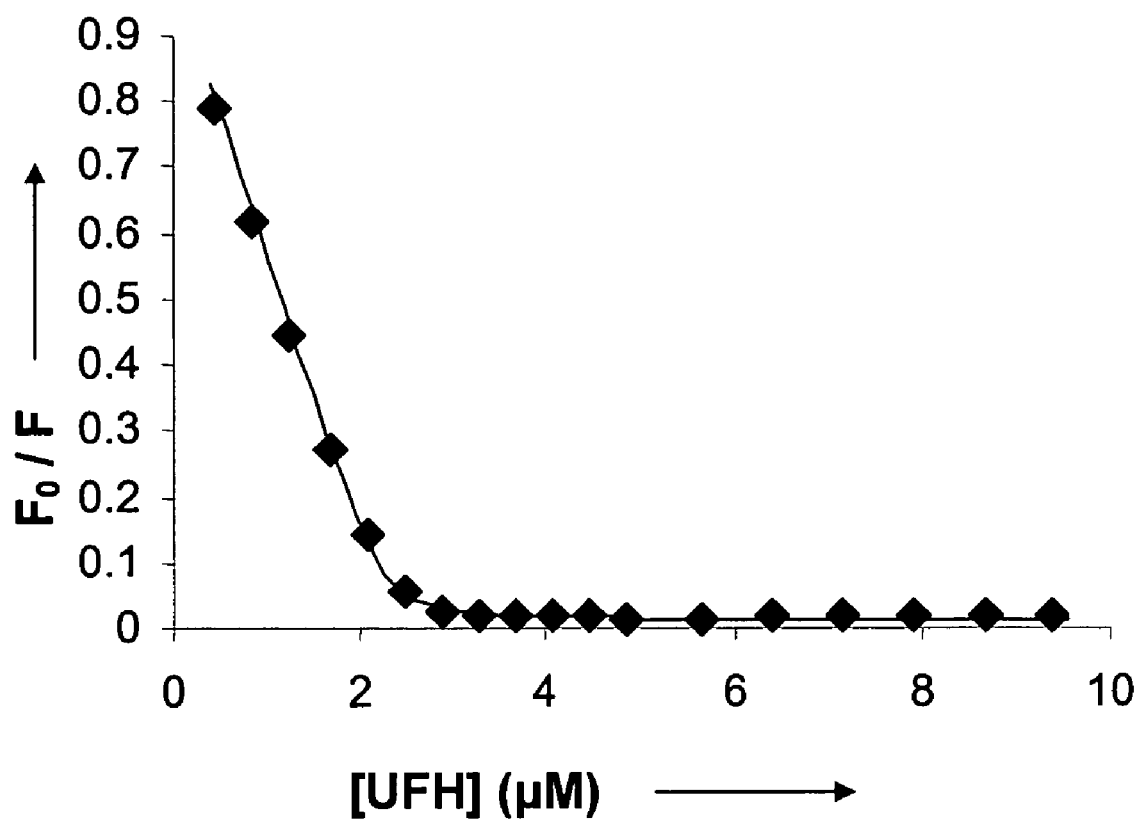
FIG. 3 is a graph showing a 1:1 binding isotherm for a synthetic receptor, according to a specific example embodiment of this disclosure, and UFH, in which the $K_a$ obtained from this curve was $1.4 \times 10^8$ M$^{-1}$.

UFH and LMWH, titrations. To determine the affinity of HR1 for UFH and LMWH, titrations of HR1 with UFH and LMWH in water buffered with 10 mM HEPES at pH=7.4 were monitored using fluorescence spectroscopy. As shown in FIG. 3, the binding of UFH and LMWH with HR1 caused a decrease in the emission spectra, resulting in a near complete quenching of the receptor's emission. By way of explanation, and not of limitation, the interaction of heparin with HR1 leads to conformational restriction of the receptor "arms," thereby modulating the fluorescence; a technique used routinely for creating chemosensors. Titration data at 357 nm was used to generate the binding isotherm, which was analyzed using a standard 1:1 binding algorithm (FIG. 3). As discussed above, due to the heterogeneous structure of heparin, one must define a repeating unit that the receptor interacts with. The binding isotherm shown in FIG. 3 was achieved by defining the concentration of heparin to be that of four saccharide units (an integral number of saccharides is not required to fit the binding isotherm). The number 4 supports a stoichiometry where each receptor on average spans four saccharide units along the heparin biopolymer. The calculated association constant between HR1 and UFH is 1.4×10$^8$ M$^{-1}$. This is an increase in affinity of near 10$^4$ for HR1 over previously prepared receptors. See Z. Zhong & E. V. Anslyn, *J. Am. Chem. Soc.*, 124:9014-15 (2002). By way of explanation, and not of limitation, the increase in affinity may be from an increase in the size of the receptor core scaffold. Furthermore, glycosaminoglycuronans, hyaluronic acid, and chondroitin-4-sulfate did not bind HR1 at low μM concentrations, among other things, further demonstrating the high selectivity of HR1 for UFH and LMWH.

Protamine titrations. Protamine sequesters heparin, thereby lowering its bioavailability to bind antithrombin III. Therefore, if there is a specific binding interaction between heparin and HR1, protamine should strip heparin that is bound to HR1, thereby restoring the fluorescence. Indeed, when analyzing either mixtures of HR1 with UFH or LMWH, fluorescence could be fully reestablished by titration of the receptor:UFH (LMWH) complex with protamine (FIG. 4(A) and FIG. 4(B)). This illustrates, among other things, that the binding between HR1 and heparin is reversible, and acts analogous to that between heparin and antithrombin III.

Calibration curves for monitoring UFH and LMWH in serum. During cardiopulmonary surgery and emergency deep venous thrombosis (DVT) conditions, heparin may be administered intravenously or subcutaneously, among other things, to prevent excessive clotting at therapeutic dosing levels of about 2 U/mL to about 8 U/mL (0.8 μM-3.2 μM). However, in postoperative and long-term anticoagulant care of DVT, patients may be treated at therapeutic dosing levels of about 0.2 U/mL to about 2 U/mL (0.08 μM-0.8 μM). To simulate monitoring conditions in a clinical setting, human and equine serums were doped with UFH and LMWH at these dosing levels. A serum sample (32 μL) doped with UFH or LMWH was added to a fluorimeter cell containing a total volume of 1.5 mL HEPES (10 mM) in deionized water. To this was added 2 μL of 1 ($2.24\times10^{-3}$ $M^{-1}$). The fluorescence stabilized over a period of 18 minutes, in contrast to the instantaneous response found in buffered water, indicating that forming the complex with heparin in serum was slow on the laboratory time scale. One nonlimiting explanation for this observation is that slower complex formation may potentially be due to the kinetics of release of heparin from natural receptors in the sera. To generate calibration curves (355 nM, FIG. 5(A) and FIG. 5(B)), emission spectra were recorded after 18 minutes for each of nine samples with varying heparin concentration. Increased levels of heparin in serum linearly correlated to lower emission responses for both UFH and LMWH within the range of clinically relevant concentrations, as was observed for the fluorimetric titrations using pure heparin in buffered water. Further, the method worked in both equine and human samples, illustrating that the affinity of the synthetic receptor for heparin may be independent of the mammalian source, and could potentially be used for, among other things, human and veterinary applications.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

What is claimed is:

1. A synthetic receptor core composition comprising at least one synthetic receptor core represented by the following formula:

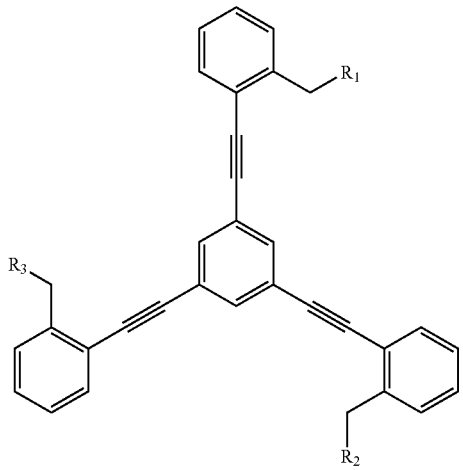

wherein $R_1$, $R_2$, and $R_3$ each independently comprise an amine group moiety.

2. The synthetic receptor core of claim 1, wherein $R_1$, $R_2$, and $R_3$ independently comprise an aldehyde or a carboxylic acid or both.

3. The synthetic receptor core of claim 1, wherein $R_1$, $R_2$, and $R_3$ independently comprise an ester.

4. The synthetic receptor core of claim 1, wherein $R_1$, $R_2$, and $R_3$ independently comprise an ether.

5. The synthetic receptor core of claim 1, wherein $R_1$, $R_2$, and $R_3$ independently comprise a hydroxyl group; wherein the hydroxyl group is converted to a good leaving group; and wherein the good leaving group undergoes a substitution reaction.

6. The synthetic receptor core of claim 1, wherein $R_1$, $R_2$, and $R_3$ independently are alkylated or arylated or both.

7. The synthetic receptor core of claim 1, wherein $R_1$, $R_2$, and $R_3$ independently are alkylated or arylated or both using alkyl halides, aryl halides, or both.

8. The synthetic receptor core of claim 1, wherein $R_1$, $R_2$, and $R_3$ independently further comprise an amide bond.

9. The synthetic receptor core of claim 1, wherein $R_1$, $R_2$, and $R_3$ independently further comprise an amino acid.

10. The synthetic receptor core of claim 1, wherein $R_1$, $R_2$, and $R_3$ independently further comprise a guanidinium.

11. The synthetic receptor core of claim 1, wherein $R_1$, $R_2$, and $R_3$ independently further comprise a spacer group.

12. The synthetic receptor core of claim 1, wherein $R_1$, $R_2$, and $R_3$ independently further comprise at least one spacer group chosen from a glutamic acid, cysteine, serine, tyrosine, lysine, histidine, threonine, and arginine.

13. The synthetic receptor core of claim 1, wherein $R_1$, $R_2$, and $R_3$ independently further comprise a diacid, such as succinic acid.

14. The synthetic receptor core of claim 1, further comprising a solid phase support.

15. The synthetic receptor core of claim 1, further comprising at least one solid phase support chosen from silica gels, resins, derivatized plastic films, multi-well assay plates, glass, glass beads, fiber optics, cotton, plastic beads, alumina gels, synthetic antigen-presenting matrices, cells, and liposomes.

16. The synthetic receptor core of claim 1, wherein the amine group moiety has the following formula:

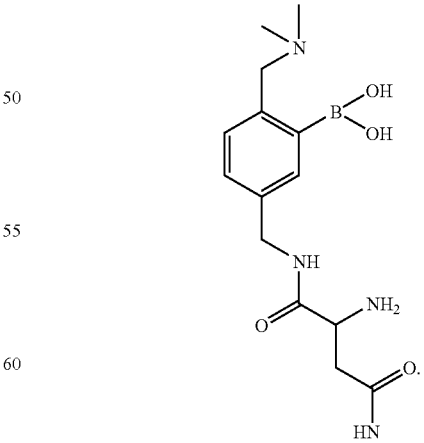

* * * * *